United States Patent [19]
Park et al.

[11] Patent Number: 6,119,532
[45] Date of Patent: Sep. 19, 2000

[54] APPARATUS AND METHOD FOR PARTICLE SAMPLING DURING SEMICONDUCTOR DEVICE MANUFACTURING

[75] Inventors: Hee-jung Park, Sungnam; Baik-soon Choi, Seoul; Jin-sung Kim, Suwon; Sung-chul Kang, Sungnam, all of Rep. of Korea

[73] Assignee: Samsung Electronics Co., Ltd., Suwon, Rep. of Korea

[21] Appl. No.: 09/081,097

[22] Filed: May 19, 1998

[30] Foreign Application Priority Data

Jun. 9, 1997 [KR] Rep. of Korea ............... 97-23701

[51] Int. Cl.$^7$ ............................................. G01N 1/22
[52] U.S. Cl. ........................... 73/864.34; 73/863.02
[58] Field of Search ....................... 73/864.34, 863.02, 73/863.21–863.25, 863.83, 863.64, 863.86, 863.03, 864.35

[56] References Cited

U.S. PATENT DOCUMENTS

| | | | |
|---|---|---|---|
| 3,973,848 | 8/1976 | Jowett et al. | 73/23.31 X |
| 4,101,282 | 7/1978 | Ririe | 73/864.35 X |
| 5,458,010 | 10/1995 | Tucina et al. | 73/864.34 X |
| 5,760,314 | 6/1998 | Bromberg et al. | 73/864.34 X |
| 5,827,744 | 10/1998 | Fose et al. | 73/864.34 X |

*Primary Examiner*—Thomas P. Noland
*Attorney, Agent, or Firm*—Jones Volentine, LLC

[57] ABSTRACT

An apparatus for sampling particles from a processing chamber used in the fabrication of semiconductor devices includes a sampling line sequentially having a sampling port, a sampling air valve, a particle sampler and an isolation valve. A pumping line is connected between the isolation valve and a pump, and a discharge line is connected between the pump and a discharge port. The apparatus includes a purge line sequentially having a purge gas source, a purge air valve, and a divergence end. A purge-sampler line connects the divergence end to the sampling line between the sampling air valve and the particle sampler, and includes a purge-sampler air valve. A purge-pump line connects the divergence end to the pumping line, and includes a purge-pump air valve. The apparatus also includes an isolation valve bypass line connected at one end to the sampling line between the particle sampler and the isolation valve, connected at the other end to the pumping line between the isolation valve and the purge-pump line, and including a bypass air valve. A control unit controls the operation of the isolation valve, the pump, and the air valves.

15 Claims, 8 Drawing Sheets

APPARATUS AND METHOD FOR PARTICLE SAMPLING DURING SEMICONDUCTOR DEVICE MANUFACTURING

BACKGROUND OF THE INVENTION

1. Field of the Invention

The present invention relates to a particle sampling apparatus and its operating method for semiconductor device manufacturing. More particularly, the present invention relates to a particle sampling apparatus for sampling particles directly from the processing chamber of a vacuum processor and its operating method.

2. Description of the Related Art

Semiconductor device manufacturing processes require very clean processing environments. Several manufacturing processes, including Low Pressure Chemical Vapor Deposition (LPCVD), Plasma Enhanced Chemical Vapor Deposition (PECVD), dry etch, sputtering, and ion injection, require a vacuum state during processing. The above processes are subject to various failures depending on the processing equipment and the corresponding processing gas used. A great number of failures of semiconductor devices are caused by particles generated in a processing chamber. In order to determine how to minimize and contain these damaging particles, it is necessary to analyze and quantify the distribution of generated particles.

Conventionally, the particles and defects present on wafers are analyzed after the wafers are processed and removed from the chamber. However, it is often impossible to determine the exact cause of the damaging particles because the particles can not be observed during the sequence of events carried out in the chamber during a process.

An impactor is one conventional device that is capable of directly sampling particles from a processing chamber. However, a drawback of the impactor is that it is designed to sample such particles only while a high pressure process is being performed in the process chamber.

Referring to FIG. 1, an impactor or particle sampler 10, collects particles by passing a gas released directly from inside the processing chamber through the sampler from the left inlet to the right outlet as designated by the arrows in FIG. 1. Particle collection wafers are placed on stages 14 and 15 oriented perpendicular to the direction of gas flow. For example, the particle sampler 10 in FIG. 1 has two stages, a first stage 14 and a second stage 15. A first nozzle 12 and a second nozzle 13 are formed facing stages 14 and 15, respectively; and nozzles 12 and 13 have different diameters.

When a pressure gradient is applied from the left inlet to the right outlet of the particle sampler 10, sample air containing particles passes through the first nozzle 12, and collides with the collecting wafer on the first stage 14 by inertia so that the particles are collected according to the speed and the mass of the particles. Then, the sample gas that collided with the first stage 14 passes through the second nozzle 13 having a smaller diameter than that of the first nozzle 12 so that the gas and particles are accelerated. The accelerated particles collide with the collecting wafer on the second stage 15. When the speed of the sample gas is sufficiently fast, very small particles will collide with, and can be collected on, the collecting wafer.

Conventionally, the impactor particle sampler is used for the collection of particles when the processing chamber is under high pressure. However, it cannot be used if the sampled gas is poisonous. If the processing gas in the processing chamber is poisonous, it must be replaced with a safer gas, such as nitrogen gas, before particle sampling is performed.

During vacuum processing, on the other hand, particle sampling can only be carried out using a vacuum pump to establish a pressure difference between the processing chamber and a pumping line downstream of the particle sampler. Particle sampling is accomplished using equipment with a sampling port that can be connected to the processing chamber, and a cut-off valve, a particle sampler, and another cut-off valve, installed in sequential order on a line from the sampling port. The sample gas is discharged through a discharge line by the vacuum pump. Then, while a vacuum process is performed in the processing chamber, the cut-off valves are opened for a certain time and some contents from the processing chamber are passed through the particle sampler where the particles are collected. The cut-off valves are then closed; then the particle sampler is disconnected from the processing chamber. Next, the collecting wafers are dismounted from the stages and particles on the collecting wafers are then analyzed.

If a vacuum process in the processing chamber is performed at a high enough vacuum, i.e., a low enough pressure, the vacuum pump of the particle collecting system can not maintain the proper pressure gradient. Then gas in the particle sampler may move in the opposite direction, carrying particles into the processing chamber. This condition is called back-flow, and it is undesirable because it increases the likelihood of damage to the semiconductor device in the processing chamber.

In addition, the particle sampler containing the collected particles must be completely purged before it is ready for subsequent use. After purging, the particle sampler must be reconnected to the processing chamber. However, the reconnecting task can again contaminate the particle sampler so that extra particles are introduced into the sampler. This can lead to a failure of the particle sampler to provide an accurate sample for analysis.

Thus there is a need for a particle sampling apparatus that can directly sample particles from a process chamber reliably, repeatedly and efficiently, whether the chamber is in a high pressure state or an extremely low pressure state. At high pressure, leaks must be prevented. At low pressure back-flow must be prevented. Purging must be leak proof and should not require disconnecting and reconnecting the apparatus to the chamber, to prevent contamination of the sampler after purging.

SUMMARY OF THE INVENTION

The present invention is directed to a particle sampling apparatus and its operating method having an internal purge system to provide reliable particle analysis. The present invention is further directed to maintaining a proper pressure difference between a high vacuum processing chamber and a pumping line. The present invention is also directed to preventing back-flow of sample gas into the processing chamber. The present invention is also directed to a particle sampling method that can be manual or automated.

To achieve these and other objects and advantages of the present invention a sampling apparatus for particle analysis comprises a sampling line including, in order, a sampling port, a sampling air valve, a particle sampler and an isolation valve, a pumping line connected between the isolation valve and a pump, and a discharge line connected between the pump and a discharge port. The apparatus includes a purge line having, in order, a purge gas source, a purge air valve, and a divergence end. A purge-sampler line connects the divergence end to the sampling line between the sampling air valve and the particle sampler, and includes a purge-sampler air valve. A purge-pump line connects the divergence end to the pumping line, and includes a purge-pump air valve. The apparatus also includes an isolation valve bypass line connected at one end to the sampling line between the particle sampler and the isolation valve, connected at the other end to the pumping line between the isolation valve and the purge-pump line, and including a bypass air valve. A control unit controls the operation of the isolation valve, the pump, and the above named air valves.

Another aspect of the present invention is a method for sampling particles from a processing chamber used in the fabrication of semiconductor devices. The method includes establishing a predetermined driving pressure inside a pumping line at a pressure level lower than a predetermined process pressure of a process gas inside a processing chamber. The next step is prepurging a particle sampler on a sampling line connected between the processing chamber and the pumping line with a purge gas by establishing flow communication both between a purge gas source on a purge line and the particle sampler and also between the particle sampler and the pumping line. The next step is reducing pressure inside the particle sampler to a level below the process pressure by terminating flow communication between the purge gas source and the particle sampler. Then the method calls for sampling the process gas for a predetermined sampling time by establishing flow communication between the processing chamber and the particle sampler. The final step is postpurging the particle sampler with the purge gas by terminating flow communication between the processing chamber and the particle sampler and establishing flow communication between the purge gas source and the particle sampler.

BRIEF DESCRIPTION OF THE DRAWINGS

The invention is described in detail with reference to the accompanying drawings in which.

DETAILED DESCRIPTION OF THE PREFERRED EMBODIMENTS

Figure 2:
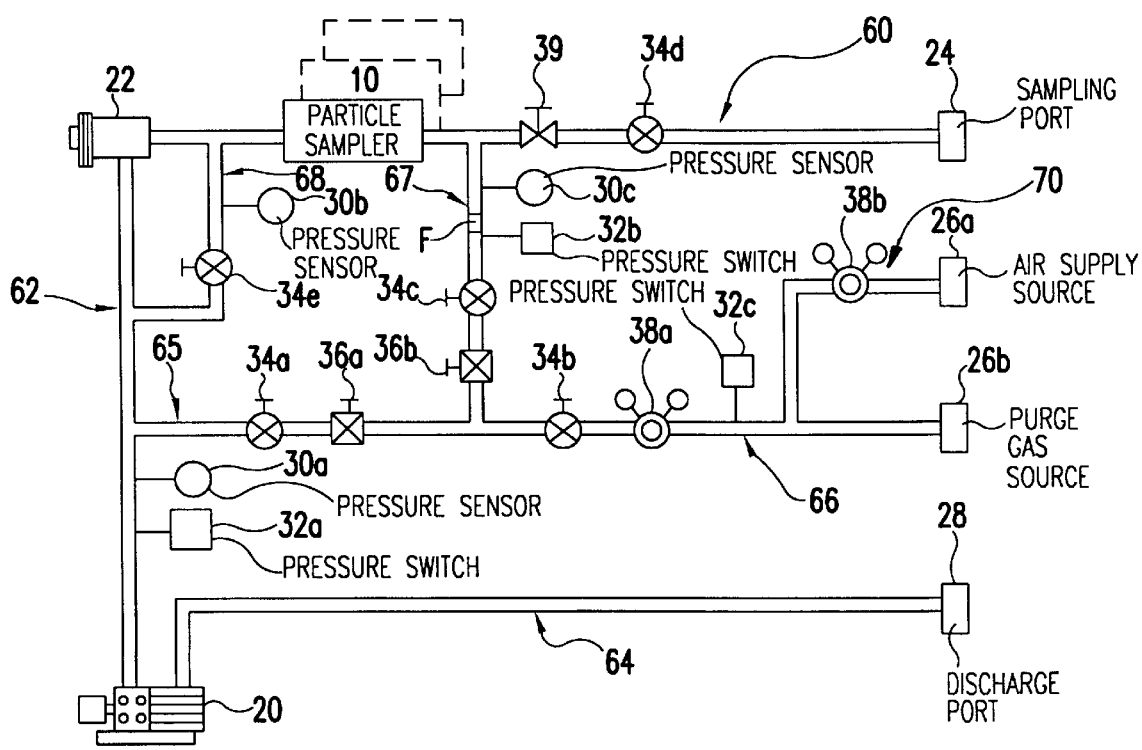
FIG. 2 is a schematic configuration of the particle sampling apparatus according to one embodiment of the present invention.

FIG. 2 is a schematic configuration of the particle sampling apparatus according to a preferred embodiment of the present invention and is used to describe the apparatus of the present invention.

Figure 3:
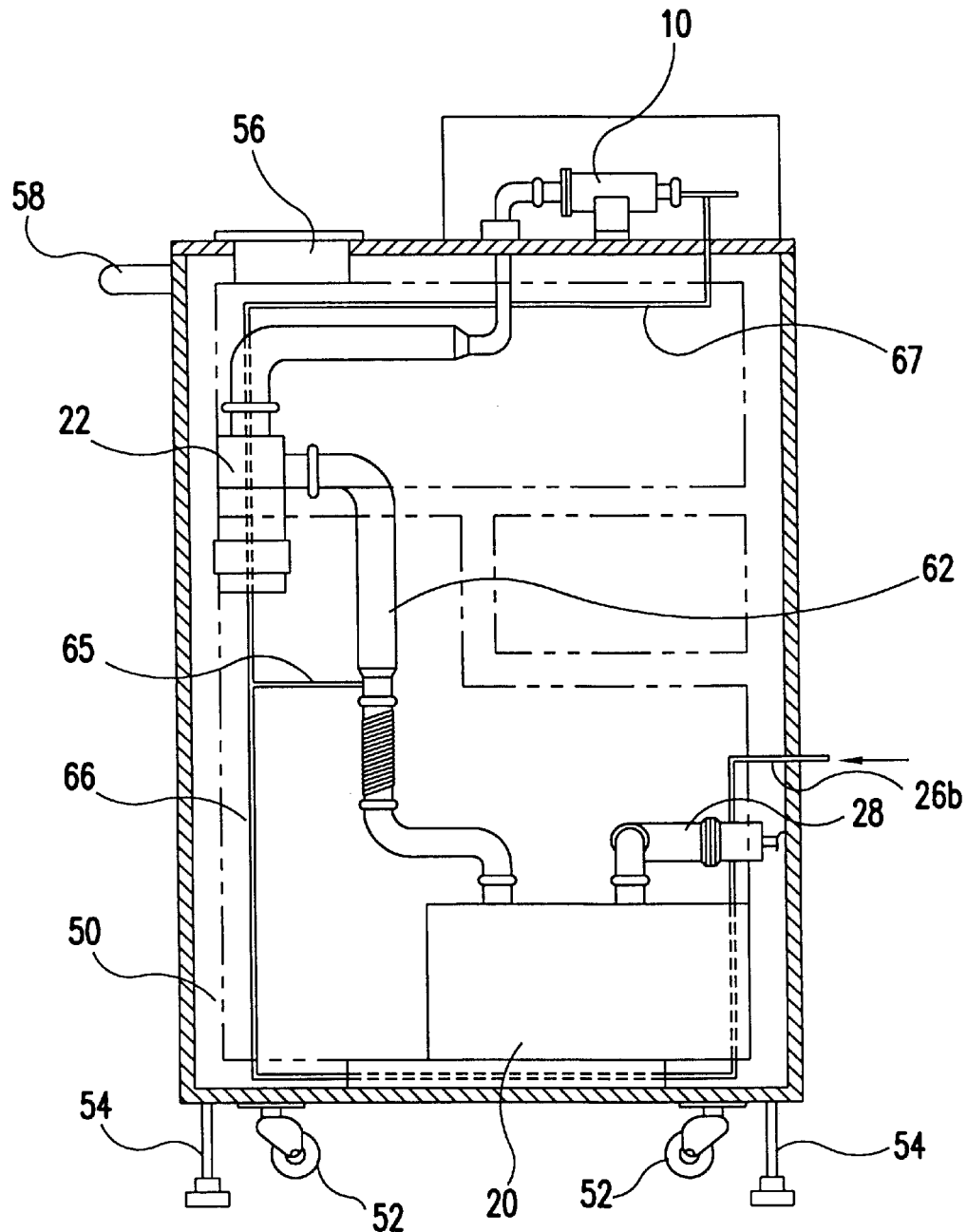
FIG. 3 is a detailed representation of an embodiment of the present particle sampling apparatus installed on a cart.

The particle sampling apparatus of the present invention includes a sampling line 60, a pumping line 62, a discharge line 64, a purge line 66, a purge-pump line 65, a purge-sampler line 67, a bypass line 68, and a control unit (56 in FIG. 3). The basic flow path for gas during particle sampling starts at the sampling port 24 (which can be connected to a processing chamber), passes via the sampling line 60 through a particle sampler 10 and into an isolation valve 22, passes via the pumping line 62 into a pumping device 20, and passes via the discharge line 64 into a discharge port 28.

The components of the sampling line 60 are first described. The sampling port 24 is for connection to a specific location on the processing chamber. In the processing chamber various vacuum process, such as LPCVD, PECVD, dry etching, ion injection or sputtering, can be performed.

A sampling air valve 34d is connected on the sampling line between the sampling port 24 and the particle sampler 10. This valve is used to control the flow of process gas from the processing chamber (not shown) to the particle sampler 10. In FIG. 2 the inlet of the particle sampler is at the right and the outlet is at the left, which is reversed from FIG. 1.

Figure 1:
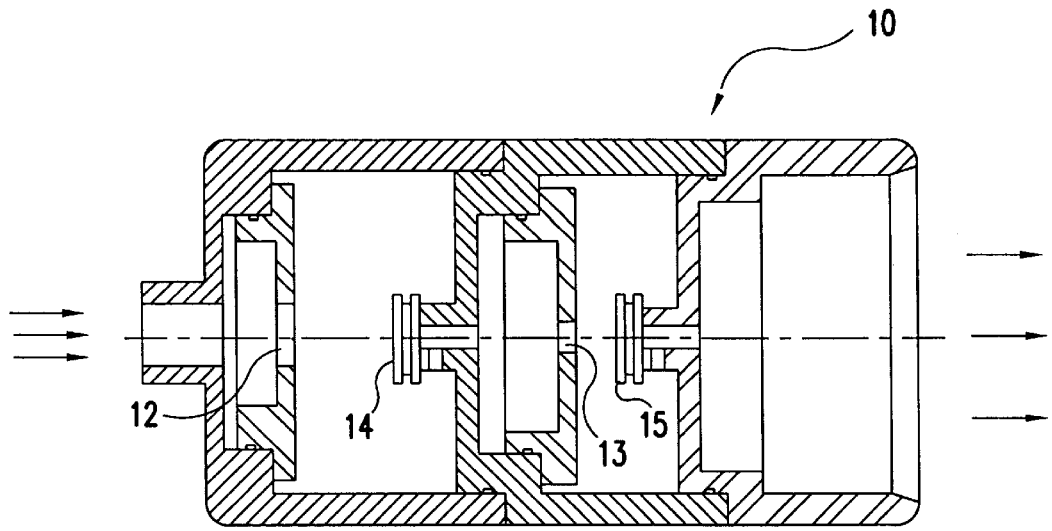
FIG. 1 is a sectional view of a prior art impactor or particle collector.

Recall that in FIG. 1 the conventional particle sampler 10 collected particles by passing gas from the inside of the processing chamber through the particle sampler. Particles are collected on wafers, for example small wafers having a size of 1 centimeter (cm) by 1 cm, placed on one or more stages 14, such as the first stage 14 and the second stage 15 in FIG. 1. Each stage 14 is oriented so that its planar area is perpendicular the direction of gas flow. A nozzle 12 faces each stage 14, for example the first nozzle 12 and the second nozzle 13 of FIG. 1 are installed on the front side of the respective stage 14 and 15. In the preferred embodiment the particle sampler 10 has a third stage (see FIG. 4) having a different diameter.

After sampling is completed the particle sampler 10 is disconnected from the particle sampling apparatus of the present invention, removed to some conventional analysis equipment, and is disassembled so that the wafers with the collected particles can be extracted. The collected particles on the wafers are then analyzed for their elements, size, and distribution, for example, by SEM (Scanning Electron Microscope) or AES (Auger Electron Spectroscopy) equipment. After the particle analysis is completed, the particle sampler 10 is again assembled with new collection wafers, and is reconnected to the particle sampling apparatus of the present invention so as to be ready to perform a new sampling process.

Referring to FIG. 2, a suitable particle sampler 10 includes the above-described two and three stage impactors, as well as an apparatus with multiple impactors arranged in parallel (dotted lines in FIG. 2). A set of parallel impactors allow the particle sampling process to be performed sequentially even when one impactor is disconnected for a separate analysis, or when particle sampling is to be separately performed at different times during a single process inside the processing chamber. Such sequential sampling is controlled by additional valves connected to the other particle samplers though any conventional means.

In the preferred embodiment, the particle sampler 10 is installed horizontally to maintain a constant flow of processing gas, with the inlet toward the sampling port 24. Leakage of sampling gas is prevented by installing a support ring (not shown) on each stage.

An isolation valve 22 is also connected on the sampling line 60 at the end opposite to the sampling port 24. In the preferred embodiment, the isolation valve 22 is a cut-off valve which performs only an on/off function. In other embodiments of the present invention, a valve that more gradually controls the amount of the gas flow can be used as the isolation valve 22. In the preferred embodiment, a manual valve 39 is also connected on the sampling line 60 between the sampling air valve 34d and the particle sampler 10.

The elements of the pumping line 62 are described next. The pumping line 62 includes a pumping device 20. In the preferred embodiment, the sampling line pumping device 20 includes a rotary pump and a turbo pump connected in series at the front end of the rotary pump. This preferred combination enables the efficient sampling of particles even during high vacuum processes in the processing chamber. Alternatively, the pumping device 20 may comprise only a rotary pump.

In some embodiments of the apparatus of the present invention, pressure sensors 30 and pressure switches 32 are included. A pressure sensor measures multiple pressure values in a range, while a pressure switch is in an "on" state up to a specific pressure and is in an "off" state at higher pressures. In the preferred embodiment the pressure sensors 30 are capacitance manometers (CM).

In the preferred embodiment, a pumping capacitance manometer (CM1) 30a and a pumping pressure switch 32a are installed on the pump line 62 between the isolation valve 22 and the pumping device 20. The CM1 30a measures a pressure value in a range from about 0 Torr (millimeters of mercury at 0° C.) to 1 Torr. The pumping pressure switch 32a is operated up to a predetermined pressure value, for example 75 Torr.

A discharge line 64 connects the pumping device 20 to the discharge port 28. No additional elements are connected to the discharge line 64.

Next are described elements on the three purge related lines, the main purge line 66, the purge-pump line 65, and the purge-sampler line 67. The purpose of the purge related lines is to clear the particle sampler 10 before and after the sampling phase of the operation using a purge gas, for example nitrogen gas.

The main purge line 66 starts from a purge gas source 26b and divides at a divergence point into a plurality of other purge related lines. A purge-sampler line 67 is connected from the divergence point to a juncture on the sampling line 60 between the particle sampler 10 and the sampling valve 34d. In the preferred embodiment, the juncture is between the particle sampler 10 and the manual valve 39. A purge-pump line 65 is connected from the divergence point to a juncture on the pumping line 62 between the isolation valve 22 and the pumping device 20. In the preferred embodiment, this juncture is between the isolation valve 22 and the pumping capacitance manometer (CM1) 30a. A purge air valve (AV2) 34b is connected on the main purge line 66, a purge-sampler air valve (AV3) 34c is connected on the purge-sampler line 67, and a purge-pump air valve (AV1) 34a is connected on the purge-pump line 65.

In the preferred embodiment, additional elements are connected on the purge related lines as follows. A purge pressure switch (PS3) 32c, a purge regulator 38a, and the purge air valve (AV2) 34b are connected on the main purge line 66, in order, from the purge gas source 26b. A purge-sampler needle valve 36b, the purge-sampler air valve (AV3) 34c, a purge-sampler pressure switch (PS2) 32b, and a purge-sampler capacitance manometer (CM3) 30c are connected on the purge-sampler line 67, in order, from the divergence point. A filter F may be installed between the purge-sampler pressure switch 32b and the purge-sampler capacitance manometer (CM3) 30c. In order, from the divergence point on the purge-pump line 65, a purge-pump needle valve 36a and the purge-pump air valve (AV1) 34a are connected. The needle valves 36 control the rate of flow of the purge gas through the purge-pump line 65 and the purge-sampler line 67. A control line 70 is connected with the purge line 66 and is used for controlling the air valves 34. The control line originates from an air supply source 26a, passes through an air regulator 38b and connects with the main purge line 66 between the purge gas source 26b and the purge pressure switch 32c.

Finally, the isolation valve bypass line 68 is described. The bypass line 68 bypasses the isolation valve 22, and connects the sampling line 60 at a point between the particle sampler 10 and the isolation valve 22 to the pumping line 62 at a juncture between the isolation valve 22 and the purge-pump line 65. The bypass line 68 includes a bypass air valve (AV5) 34e. In the preferred embodiment, the bypass line 68 has connected, in order from the sampling line 60, a bypass capacitance manometer (CM2) 30b and the bypass air valve (AV5) 34e.

The pumping device 20, isolation valve 22, and air valves 34 can be controlled manually or automatically. In the preferred embodiment, every element of the particle sampling apparatus, including, for example, each air valve 34, isolation valve 22, and pumping device 20, is automatically controlled by a control unit (56 in FIG. 3).

FIG. 3 is a detailed representation of one embodiment of the present particle sampling apparatus including a cart. The elements of the particle sampling apparatus of FIG. 2 are contained inside a frame 50, having for example a hexahedron-shape, and a plurality of rollers 52 fixed under the frame 50 to enable movement. In addition, the particle sampling apparatus can be fixed in position by extending a plurality of supports 54. A knob 58 is formed on the upper side of the frame 50. The particle sampler 10 is mounted horizontally on the top side of the frame 50, the pumping device 20 is mounted on the bottom of the frame 50, the isolation valve 22 is mounted vertically inside the frame 50, and the pumping line 62, the purge line 66, the purge-pump line 65, and the purge-sampler line 67 are all within the frame 50. A control unit 56, such as an LED-touch screen, is formed on the top side of the frame disposed toward knob 58. In the control unit 56, all actuators such as valves are controlled manually or automatically. The purge gas source 26b and the discharge port 28 pass through a side of the frame 50.

Figure 4:
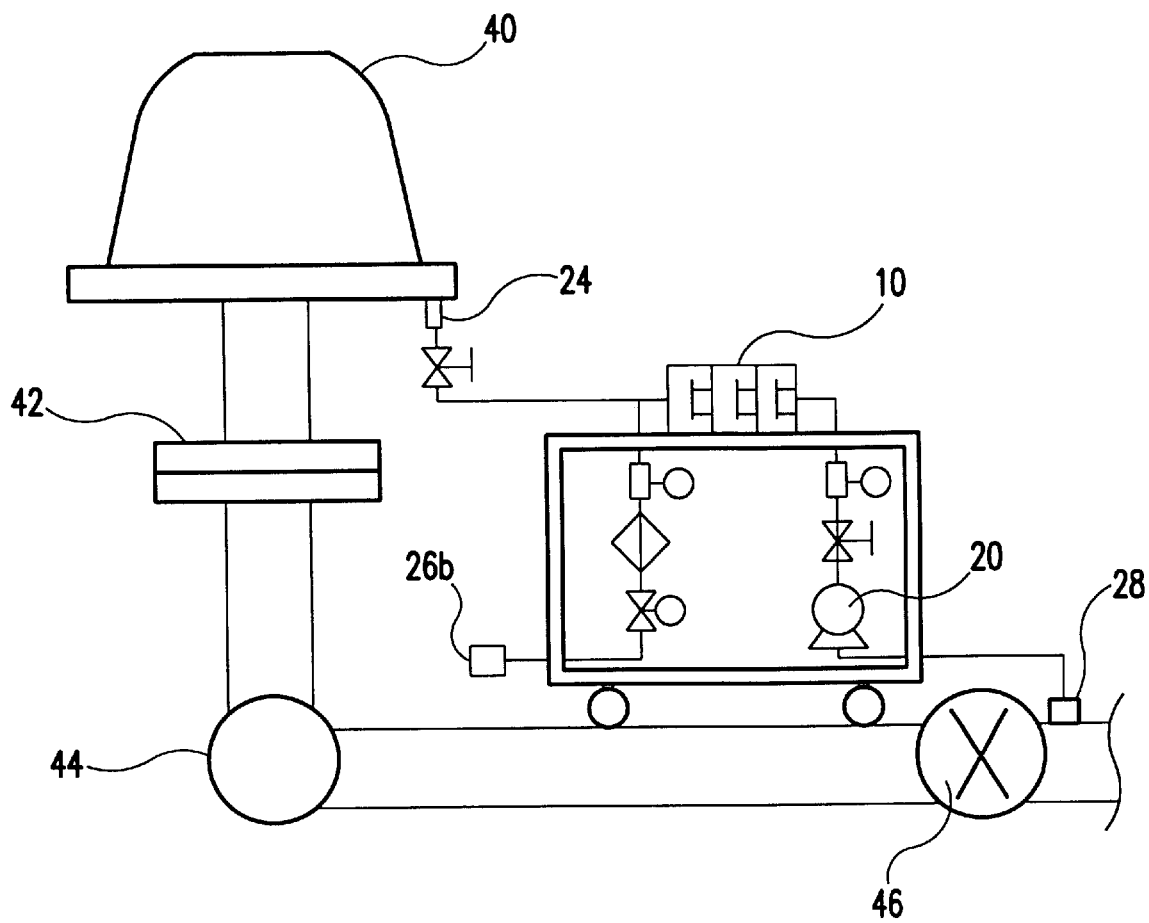
FIG. 4 is a schematic representation of the particle sampling apparatus according to an embodiment of the present invention employed with a semiconductor device manufacturing system.

FIG. 4 is a schematic representation of the particle sampling apparatus according to an embodiment of the present invention employed with a semiconductor device manufacturing system. Sampling port 24 is coupled at one end to a processing chamber 40. Sampling gas is pumped through a particle sampler 10, a pumping device 20, and a discharge port 28. Purge gas is supplied from a purge gas supply source 26*b* to the sampling apparatus. A throttle valve 42, a turbo pump 44, and a rotary pump 46 are installed in order from the lower end of the processing chamber 40 to maintain the processing chamber 40 in a vacuum state. The pumping device 20 may comprise a turbo pump and a rotary pump to balance the vacuum pressures of the sampling apparatus with those of the processing chamber.

In the preferred embodiment, the actuators of the pumping device 20, the isolation valve 22, and the various air valves 34 are interlocked to provide stable processing and to prevent damage. Referring to FIG. 2, the interlocking relationships are described specifically in the following. The pumping device 20 is interlocked with the isolation valve 22 such that the pumping device 20 is "on", i.e., the pumping device 20 is running, when the isolation valve 22 is open. Likewise, the pumping device 20 is interlocked to an "on" position when either the sampling air valve 34*d* or the bypass air valve 34*e* is open. The isolation valve 22 is not closed when the sampling air valve 34*d* is open or when the purge and the purge-sampler air valves 34*b* and 34*c* are open, and the isolation valve 22 is interlocked to a closed position when the pumping device 20 is off. The purge-pump air valve 34*a* is interlocked to a closed position when the isolation valve 22 is open, or when the bypass air valve 34*e* or the purge-sampler air valve 34*c* is open. The purge air valve 34*b* is interlocked to a closed position when the sampling air valve 34*d* is open. The purge-sampler air valve 34*c* is interlocked to a closed position when the purge-pump air valve 34*a* is open. The sampling air valve 34*d* is interlocked to a closed position when the purge-pump, the purge, and the purge-sampler air valves 34*a*, 34*b*, and 34*c* are open; when the isolation valve 22 is closed; or when the pumping device 20 is "on" with the pressure of the bypass capacitance manometer (CM2) 30*b* higher than the process pressure and the purge-sampler pressure switch 32*b* "on". The bypass air valve 34*e* is interlocked to a closed position when the purge and purge-sampler air valves 34*b* and 34*c* are open, and the pumping device 20 is operating.

The operating method of the present invention includes preparation for establishing a driving pressure, prepurge for clearing out the particle sampler with a purge gas, pumping for reducing the pressure in the particle sampler, sampling for passing the process gas from the processing chamber into the particle sampler, and postpurge for clearing the process gas out of the particle sampler. After these steps the particle sampling method is complete. Referring to FIG. 5 through FIG. 9 and to FIG. 2, the preferred embodiment of the operating method according to the present invention is illustrated in detail.

Figure 5:
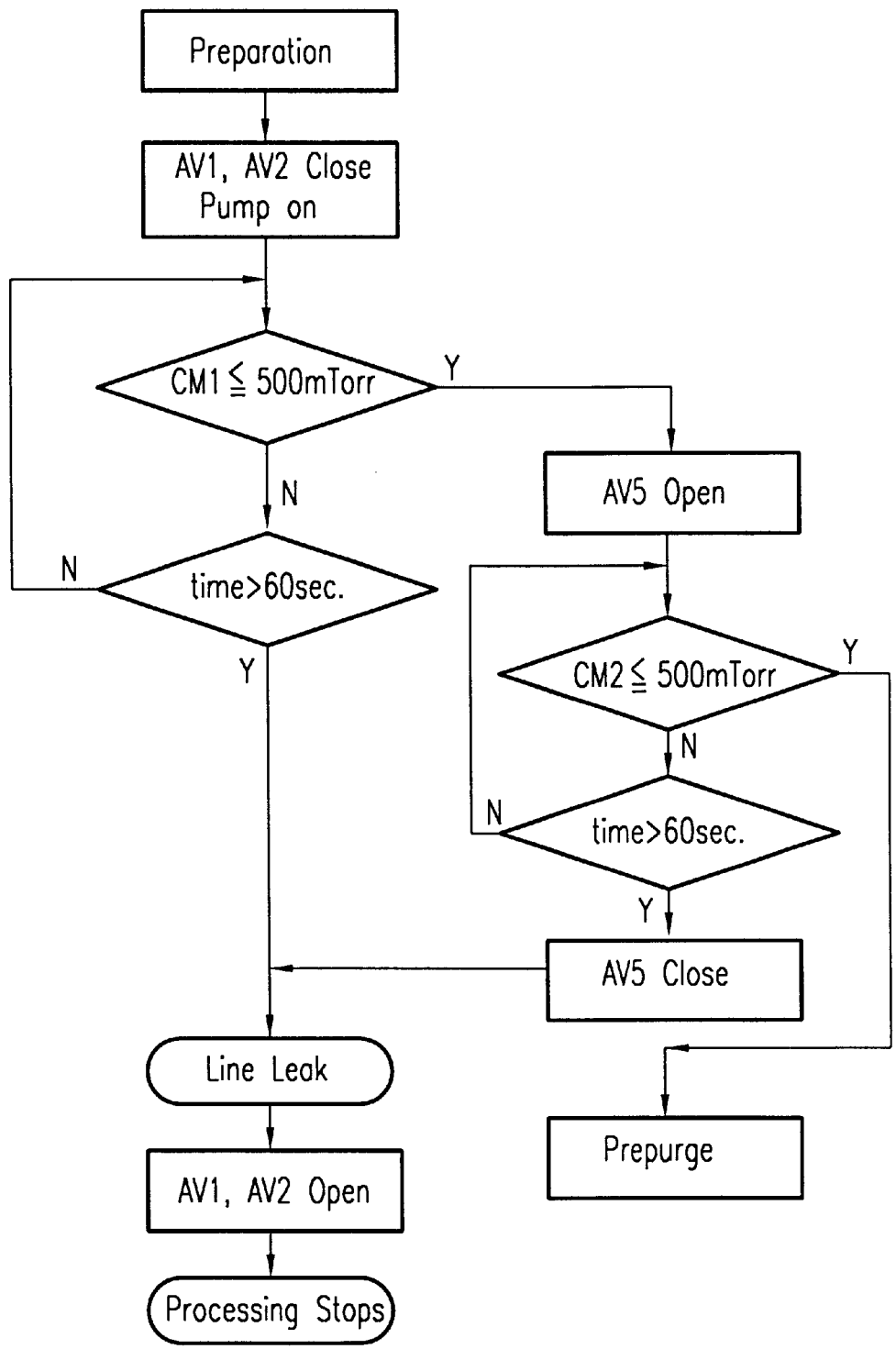
FIG. 5 is a flow chart illustrating a method for operating the particle sampling apparatus of the present invention during the preparation (establishing) step according to an embodiment of the present method invention.

FIG. 5 illustrates the preferred embodiment of the preparation step in which a driving pressure is established in the pumping line. First the purge-pump air valve (AV1) 34*a* and the purge air valve (AV2) 34*b* are closed, and the pumping device 20 is turned "on". If a pump-line pressure measured by the purge-pump pressure sensor (CM1) 30*a*, for example a capacitance manometer, falls to a predetermined driving pressure, for example 500 milliTorr (mTorr), then an adequate vacuum exists to continue processing and the bypass air valve 34*e* is opened. A pumping period of time is measured from the start of the pumping using a timer within the control unit. If the pump-line pressure does not fall to the driving pressure, for example 500 mTorr, while the pumping period is less than or equal to a predetermined maximum pumping time, for example 60 seconds, a leak in the pumping line 62 is indicated and so processing does not continue. In this case the method ceases and the purge-pump air valve (AV1) 34*a* and the purge air valve (AV2) 34*b* are opened.

When the pump-line pressure measured by CM1 30*b* is at or below the driving pressure, the bypass air valve (AV5) 34*e* is opened and the part of the sampling line 60 including the particle sampler 10 is evacuated by pumping through the bypass line 68. If a bypass pressure measured by the bypass pressure sensor (CM2) 30*b*, for example a capacitance manometer, also falls to the driving pressure, for example 500 mTorr, the preparation step is complete and the prepurge step begins. A bypass pumping period of time is measured from the start of the bypass pumping using the timer. If the bypass pressure does not fall to the driving pressure, for example 500 mTorr, while the bypass pumping period is less than or equal to the predetermined maximum pumping time, for example 60 seconds, a leak in the sampling line 62 is indicated and so processing does not continue. In this case the method ceases and the purge-pump air valve (AV1) 34*a* and the purge air valve (AV2) 34*b* are opened.

Figure 6:
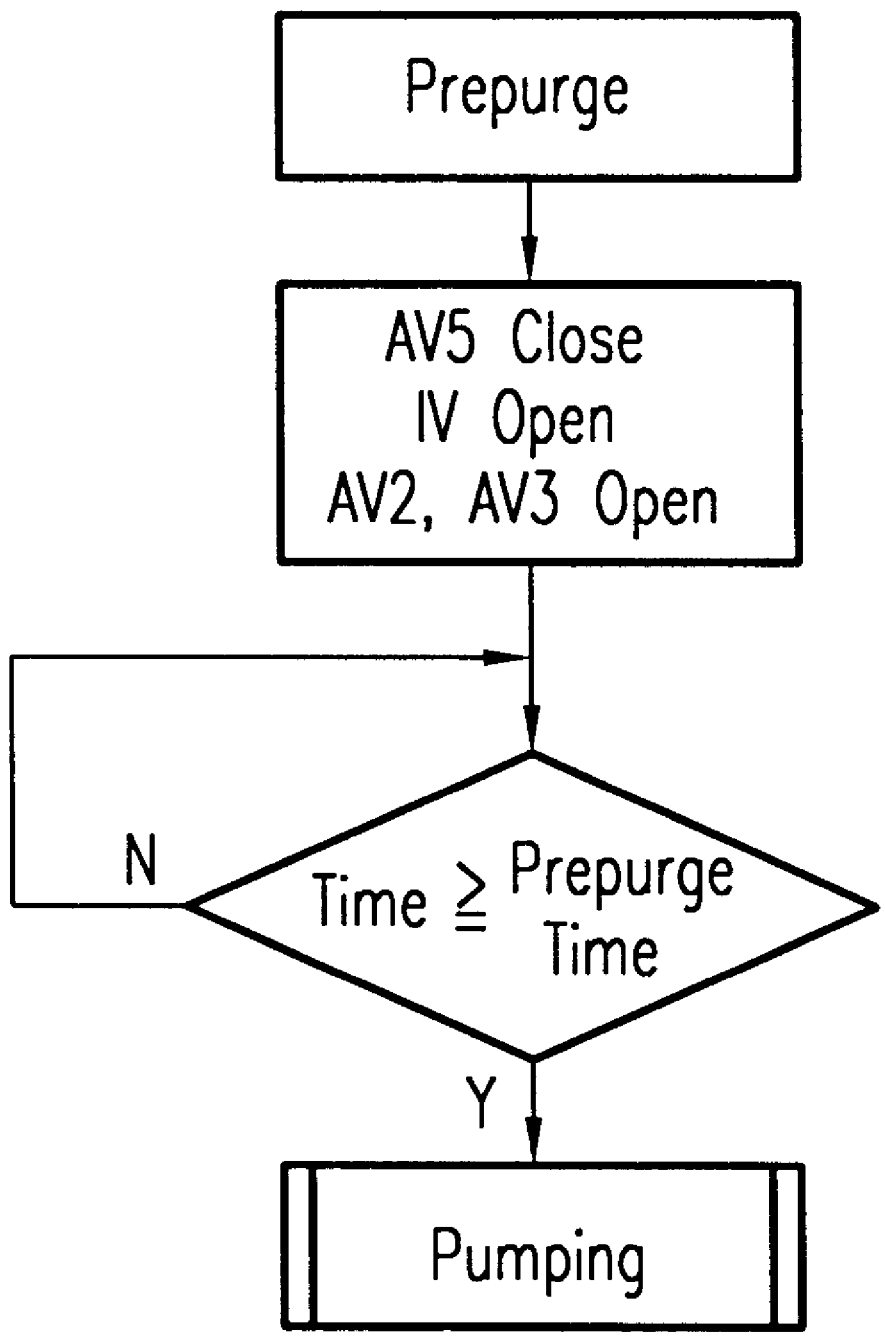
FIG. 6 is a flow chart illustrating a method for operating the particle sampling apparatus of the present invention during the prepurge step according to an embodiment of the present method invention.

FIG. 6 is a flow chart illustrating the preferred embodiment of the present method during the prepurge step, i.e., from the start of the prepurge step to the start of the pumping (reducing) step. The prepurge step is carried out by closing the bypass air valve (AV5) 34*e*, opening the isolation valve (IV) 22, and opening the purge air valve (AV2) 34*b* and the purge-sampler air valve (AV3) 34*c*. These operations allow a purge gas, such as nitrogen gas substantially free of particles, to flow from the purge gas source 26*b* into the particle sampler 10 and clear it out. The prepurge step continues until a prepurge period, begun when the above air valves are opened, reaches a predetermined prepurge time. At that time prepurge is complete. Thereafter the pumping (reducing) process follows.

Figure 7:
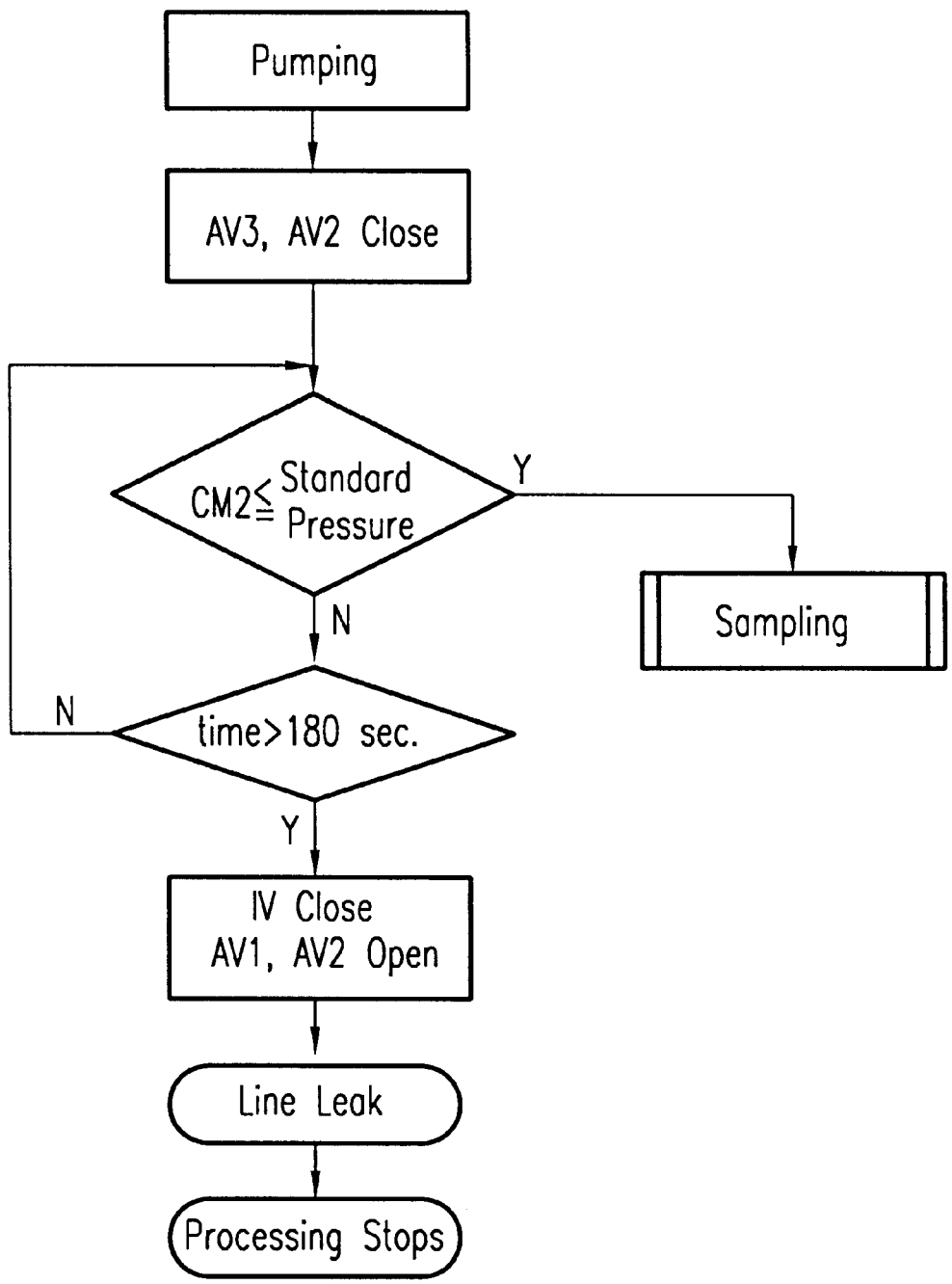
FIG. 7 is a flow chart illustrating a method for operating the particle sampling apparatus of the present invention during the pumping (reducing) step according to an embodiment of the present method invention.

FIG. 7 is a flow chart illustrating the preferred embodiment of the present method during the pumping (reducing) step, i.e., from the beginning of the pumping (reducing) step to the beginning of the sampling step. After normal completion of prepurge and pumping (reducing), the sampling starts. The pumping (reducing) step starts by closing the purge-sampler air valve (AV3) 34*c* and the purge air valve (AV2) 34*b*. Successful sampling requires that the pressure at the outlet of the particle sampler, measured as a reducing pressure by the bypass pressure sensor (CM2) 30*b*, for example a capacitance manometer, is below the predetermined process pressure (also called a "standard pressure") inside the processing chamber. The purpose of the reducing step is to achieve this process pressure at the bypass pressure sensor (CM2) 30*b* by pumping with the pumping device 20. When the reducing pressure measured by the bypass pressure sensor (CM2) 30*b* falls to the process pressure or below, reducing is complete and sampling begins. However, a timer is initiated to measure a reducing period from the time of the opening of air valves 34*c* and 34*b*. When the pressure fails to fall below the process pressure by the time the reducing period exceeds a predetermined maximum reduction time, for example 180 seconds, the failure is indicative of a leak in the pumping line or sampling line, so processing does not continue. In this case the method ceases; the isolation valve 22 is closed, and the purge-pump air valve (AV1) 34*a* and the purge air valve (AV2) 34*b* are opened.

Figure 8:
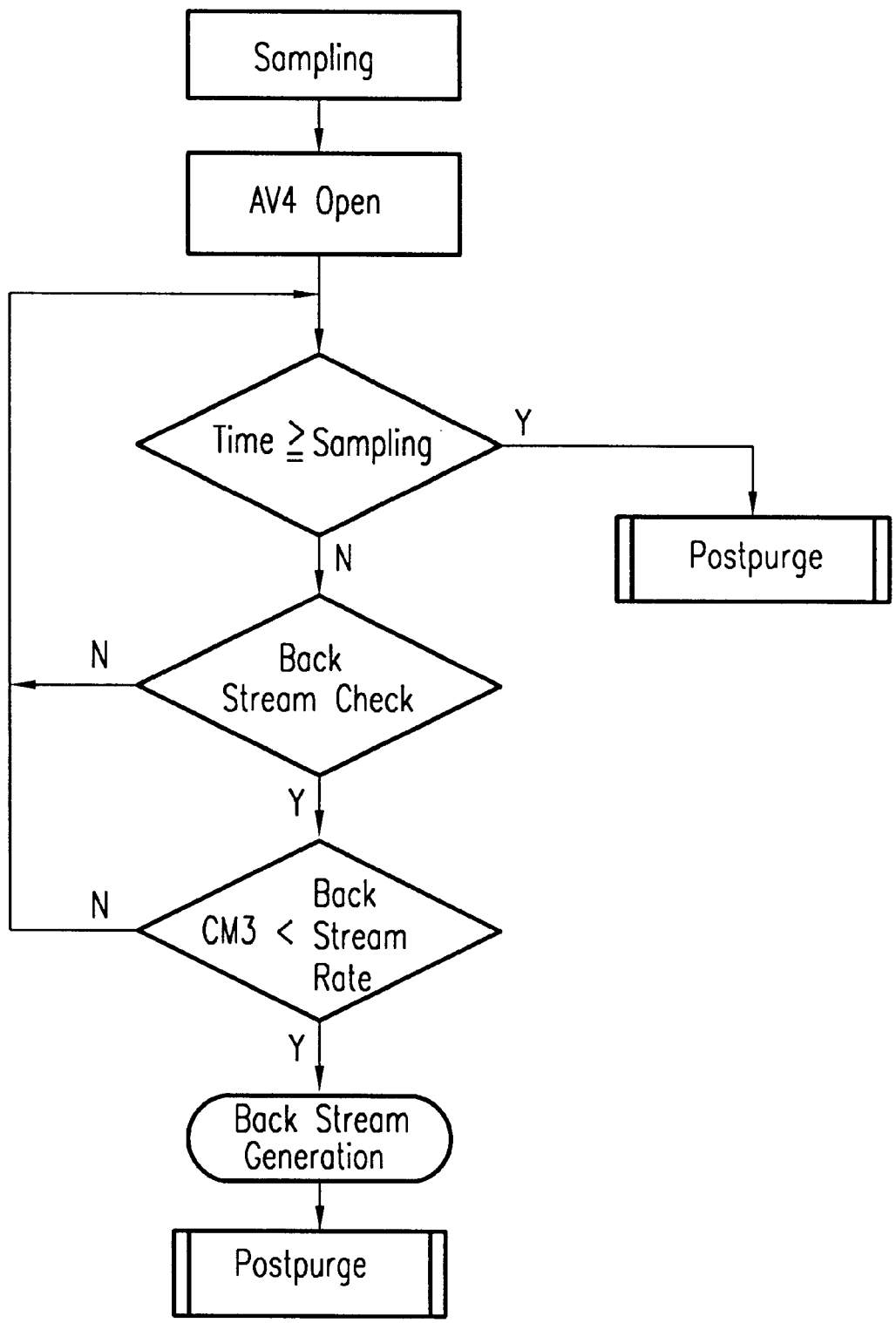
FIG. 8 is a flow chart illustrating a method for operating the particle sampling apparatus of the present invention during the sampling step according to an embodiment of the present method invention.

FIG. 8 is a flow chart illustrating the preferred embodiment of the present method during the sampling step, i.e., from the beginning of the sampling step to the beginning of the postpurging step. The sampling process begins when the sampling air valve (AV4) 34*d* is opened which allows process gas to enter the particle sampler 10, driven by the difference in the process pressure of the processing chamber and the reducing pressure. A timer is initiated to measure a sampling period when the sampling valve is opened. When the sampling period exceeds a predetermined sampling time set up by the processing recipe, the sampling is completed normally. However, the sampling is stopped before the sampling period exceeds the predetermined sampling time if any back flow is detected. In the preferred embodiment checking the back flow is optional. If back flow is checked, it is done using the purge-sampler pressure sensor (CM3) 30c to monitor a back pressure. A back stream rate is set up in the processing recipe. The back stream rate is a pressure determined in relation to the process pressure and a rate established by the processing recipe (process pressure—process pressure/rate). If the back pressure ever equals or exceeds the back stream rate during the sampling time, conditions favor back flow and there is danger that gas will flow from the particle sampler back to the process chamber. Therefore, if back flow is checked and the back pressure equals or exceeds the back stream rate during the sampling time, the sampling step is treated as complete.

Figure 9:
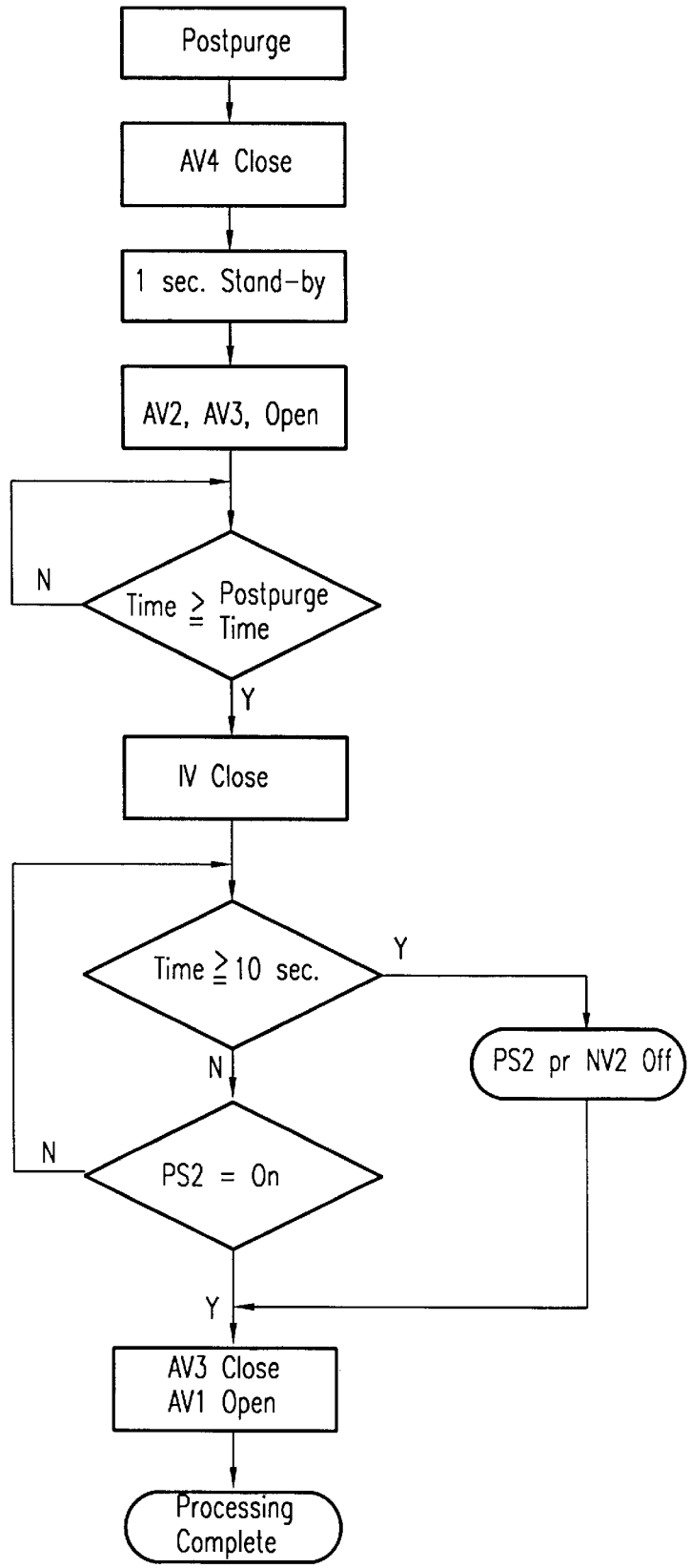
FIG. 9 is a flow chart illustrating a method for operating the particle sampling apparatus of the present invention during the postpurging step according to an embodiment of the present method invention.

FIG. 9 is a flow chart illustrating the preferred embodiment of the present method during the postpurge step, i.e., from the beginning of the postpurge step to the completion of processing. The sampling air valve (AV4) 34d is closed to stop the flow of process gas and terminate sampling and a timer is initiated to measure a stand-by period. Then, when the stand-by period exceeds a predetermined stand-by time, for example 1 second, the purge air valve 34b and the purge-sampler air valve 34c are opened to allow purge gas to enter the sampling line and the particle sampler. The stand-by time serves to prevent the occurrence of a back stream of purge gas into the processing chamber.

A timer is initiated to measure a postpurge period beginning upon the opening of the purge air valve 34b and the purge-sampler air valve 34c. In this state, purge gas is driven through the particle sampler 10 by the pumping device 20. When the postpurge period exceeds a predetermined postpurge time as set up in the processing recipe, the isolation valve 22 is closed. This terminates the pumping of the purge gas through the particle sampler 10 and should lead to the build up of purge gas and purge gas pressure in the sampling line. This is desirable to eliminate the vacuum in the sampling line 60 and bring both the sampling line 60 and the particle sampler 10 up to target pressure near the ambient room pressure before disconnecting the particle sampler 10. To ensure pressure in the sampling line 60 and particle sampler 10 reach the target pressure, either the purge-sampler pressure switch (PS2) 32b must detect a pressure above the target pressure and close the purge-sampler needle valve (NV2) 36b, or the postpurge step must pause a predetermined switch time, for example 10 seconds, after closing the isolation valve 22. A timer is initiated to measure a switching period when the isolation valve 22 is closed.

If the switching period equals or exceeds the predetermined switching time, then the purge-sampler pressure switch (PS2) 32b turns off, or the purge-sampler needle valve (NV2) 36b opens. Then the purge-sampler air valve 34c closes, the purge-pump air valve 34a opens, and the process is complete at the predetermined switching time.

If the second pressure switch (PS2) 32b is on while the switching period is less than the predetermined switching time, the purge-sampler air valve 34c is closed, and the purge-pump air valve 34a is open, and processing is complete at this time, earlier than the predetermined switching time.

After completion of the particle sampling the processing is complete and the particle sampler 10 is disconnected from the apparatus, removed, and disassembled for particle analysis.

Accordingly, the present invention including an internal purge system provides for improved particle analysis. In addition, the present invention including an internal pump, allows the particle sampling to be carried out even during vacuum processing conditions inside the processing chamber thereby providing accurate particle analysis for a broader range of semiconductor device fabrication processes. Further, since the back stream of sampling gas into the processing chamber is prevented during sampling, particle sampling is carried out without increasing the likelihood of malfunctions in the processing chamber which adversely affect the semiconductor devices.

While preferred embodiments of the present invention have been described, it will be understood by those skilled in the art that various changes and modifications may be made, and equivalents may be substituted for elements thereof, without departing from the true scope and spirit of the present invention. Therefore, it is intended that the present invention not be limited to the particular embodiments disclosed, but that the present invention include all embodiments falling within the scope of the appended claims and their equivalents.

What is claimed is:

1. An apparatus for sampling particles, comprising:
   a sampling line sequentially including a sampling port, a sampling air valve, a particle sampler and an isolation valve;
   a pumping line connected between the isolation valve and a pump;
   a discharge line connected between the pump and a discharge port;
   a purge line sequentially including a purge gas source, a purge air valve, and a divergence end;
   a purge-sampler line connecting the divergence end to the sampling line between the sampling air valve and the particle sampler, and including a purge-sampler air valve;
   a purge-pump line connecting the divergence end to the pumping line, and including a purge-pump air valve;
   an isolation valve bypass line connected at one end to the sampling line between the particle sampler and the isolation valve, connected at the other end to the pumping line between the isolation valve and the purge-pump line, and including a bypass air valve; and
   a control unit for controlling the operation of the isolation valve, the pump, the sampling air valve, the purge air valve, the purge-sampler air valve, the purge-pump air valve, and the bypass air valve.

2. The apparatus of claim 1, further comprising a manual valve connected on the sampling line between the sampling air valve and the purge-sampler line.

3. The apparatus of claim 1, further comprising a purge regulator connected on the purge line between the purge gas source and the purge air valve.

4. The apparatus of claim 1, further comprising:
   a purge-pump needle valve connected on the purge-pump line between the divergence end and the purge-pump air valve, and
   a purge-sampler needle valve connected on the purge-sampler line between the divergence end and the purge-sampler air valve.

5. The apparatus of claim 1, further comprising an additional particle sampler connected on the sampling line in parallel with the particle sampler.

6. The apparatus of claim 1, the particle sampler comprising three stages oriented to be perpendicular to a horizontal flow of a sample gas.

7. The apparatus of claim 1, further comprising a filter inside the purgesampler line.

8. The apparatus of claim 1, further comprising:
a pumping pressure switch connected on the pumping line;
a purge-sampler pressure switch connected on the purge-sampler line between the purge-sampler air valve and the sampling line; and
a purge pressure switch connected on the purge line between the purge gas source and the purge air valve.

9. The apparatus of claim 1, further comprising a movable cart for holding the sampling line, the pumping line, the discharge line, the purge line, the purge-sampler line, the purge-pump line, the bypass line, and the control unit.

10. The apparatus of claim 1, further comprising:
a pumping pressure sensor connected on the pumping line;
a bypass pressure sensor connected on the bypass line between the sampling line and the bypass air valve; and
a purge-sampler pressure sensor connected on the purge-sampler line between the sampling line and the purge-sampler air valve.

11. The apparatus of claim 10, wherein the pumping pressure sensor, the bypass pressure sensor, and the purge-sampler pressure sensor are capacitance manometers.

12. The apparatus of claim 11, the pump further comprising a turbo pump connected between the pumping line and the rotary pump.

13. The apparatus of claim 12, further comprising a chamber vacuum pump connected to the vacuum chamber for maintaining a process gas inside the vacuum chamber at a predetermined process pressure.

14. The apparatus of claim 1, wherein the pump comprises a rotary pump.

15. The apparatus of claim 1, further comprising a vacuum chamber connected to the sampling port for the fabrication of a semiconductor device.

* * * * *